(12) United States Patent
Mosbach

(10) Patent No.: US 6,489,418 B1
(45) Date of Patent: Dec. 3, 2002

(54) PREPARATION AND APPLICATION OF ARTIFICIAL ANTI-IDIOTYPIC IMPRINTS

(76) Inventor: Klaus Mosbach, Pl. 5548, Lackalänga 31, S-244 94 Furulund (SE)

(*) Notice: Subject to any disclaimer, the term of this patent is extended or adjusted under 35 U.S.C. 154(b) by 0 days.

(21) Appl. No.: 08/626,342

(22) Filed: Apr. 2, 1996

Related U.S. Application Data (63) Continuation of application No. PCT/SE95/00135, filed on Feb. 10, 1995.

(30) Foreign Application Priority Data

Feb. 10, 1994 (SE) .............................................. 9400450

(51) Int. Cl.$^7$ .................................................. C08J 5/00
(52) U.S. Cl. .................... 526/238.1; 264/108; 264/219; 264/220; 264/221; 264/225; 264/226; 264/227; 264/330; 264/DIG. 44; 264/330.11; 264/331.16; 264/331.19; 424/78.08; 424/78.37; 526/238.2; 435/183; 435/188.5; 530/387.1; 530/388.1; 530/388.9; 530/389.8
(58) Field of Search .............................. 264/108, 219, 264/220, 221, 225, 226, 227, 330, DIG. 44, 330.11, 331.16, 331.19; 424/78.08, 78.37; 526/238.1, 238.2; 435/183, 188.5; 530/387.1, 388.1, 388.9, 389.8

(56) References Cited

U.S. PATENT DOCUMENTS 4,447,374 A * 5/1984 Tanaka ......................... 264/22
5,110,833 A 5/1992 Mosbach ..................... 521/50

OTHER PUBLICATIONS

"Insulin's Structure as a Modified and Monomeric Molecule", Ru Chang Bi et al., *Bipolymers,* vol. 23, pp. 391–395 (1984).

"Structure and Stability of Insulin Dissolved in 1–Octanol", James Matsuura et al., *J. Am. Chem. Soc.,* 1993, vol. 115, pp. 1261–1264.

* cited by examiner

*Primary Examiner*—Frederick Krass
(74) *Attorney, Agent, or Firm*—Burns, Doane, Swecker, & Mathis, LLP (57) ABSTRACT

This patent application describes the use of molecular imprinting as a means for preparation of anti-idiotypic imprint matrices. With this technique, imprints of artificial or natural molecules including their recognition sites, such as of molecularly imprinted polymers or biological receptors, antibodies or enzymes, can be prepared. In the former case, using the original imprints as casts or molds in a subsequent polymerisation step, utilising preferentially functionally complementary monomers, the formation of imprint materials containing recognition sites complementary in shape and functionality with the original imprint can be obtained but being of different composition. Alternatively, imprints or images of the artificial or biological species can be obtained directly. The so formed preparations can be used in a vast variety of applications, e.g. as new drugs, inhibitors or new affinity materials.

24 Claims, 6 Drawing Sheets

PREPARATION AND APPLICATION OF ARTIFICIAL ANTI-IDIOTYPIC IMPRINTS

This application claims the benefit of priority under 35 U.S.C. 120 of PCT/SE95/00135, filed Feb. 10, 1995.

The present invention concerns the preparation and application of artificial anti-idiotypic antibodies obtained by molecular imprinting.

It is known from Nature that antibodies can in their turn give rise to anti-antibodies. Such anti-antibodies or anti-idiotypic antibodies have been investigated widely [1]. The combining site of an anti-idiotypic antibody may display structural features which may be the "internal image" of the original antigen (the previous antibody). Attempts have also been described lately of producing monoclonal anti-idiotypic antibodies being functional internal images of enzyme active sites leading in one case to the formation of a catalytic antibody with cholinesterase activity [2]. This was carried out by allowing an antibody raised against an enzyme, i.e. cholinesterase, to be injected resulting in the aforementioned anti-anti-bodies.

Figure 1:
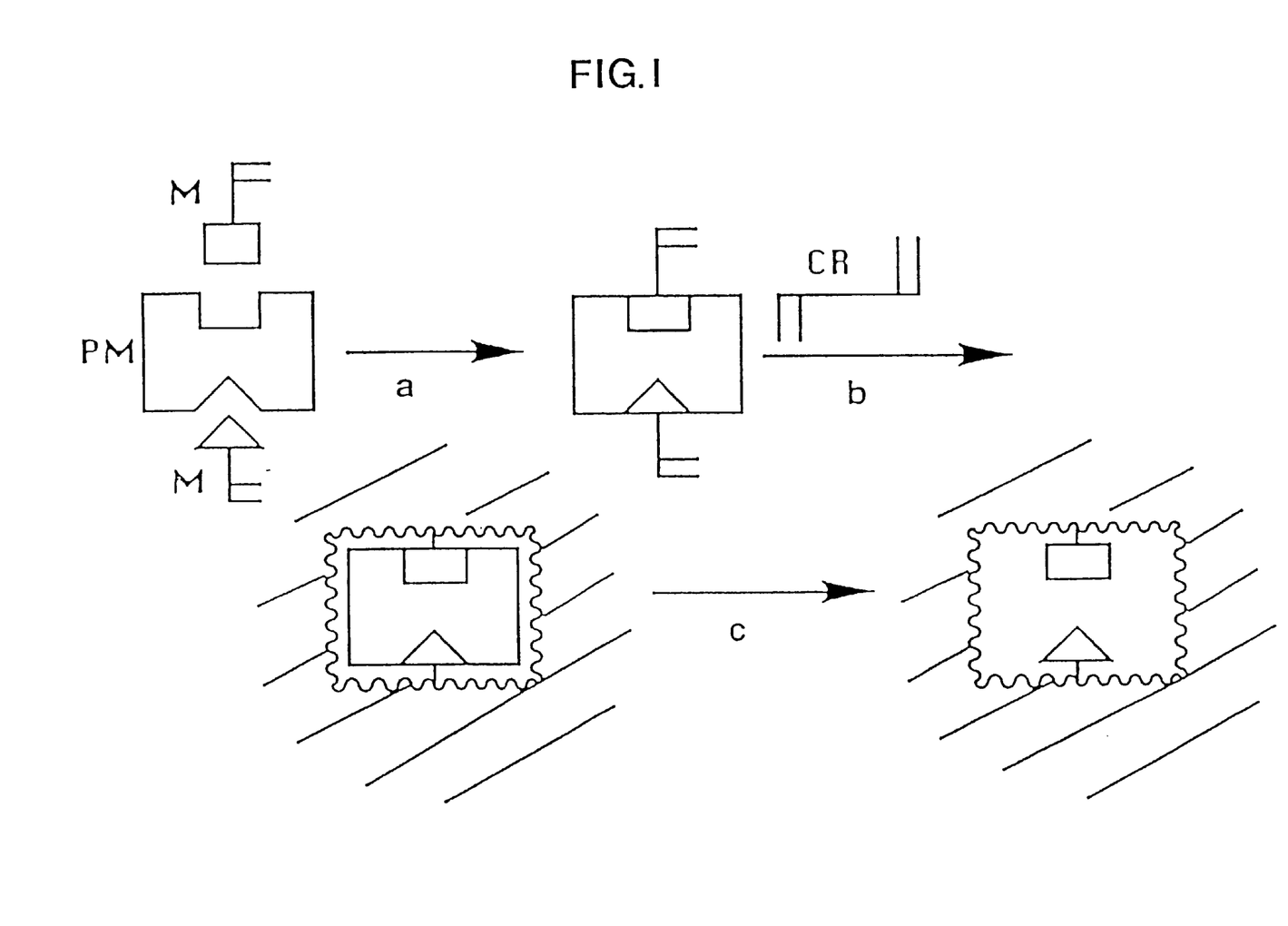
FIG. 1 shows the principle of molecular imprinting. Development of complementary interactions between the print molecule and the monomers (a); polymerisation (b); removal of the print molecule from the polymer (c). M, monomers; PM, print molecule; CR, crosslinker.

A more presently developed technique, that of molecular imprinting, is a major element for the here described invention [3, 4]. It is the name given to a process for preparing polymers that are selective for a particular compound (the print molecule). The technique involves: (1) prearranging the print molecule and the monomers and allowing complementary interactions (non-covalent or reversible covalent) to develop; (2) polymerising around the print molecule-monomer complex; and (3) removing the print molecule from the polymer by extraction (FIG. 1). Polymerisation thus preserves the complementarity to the print molecule and the polymer will selectively adsorb the print molecule subsequently. The technique has also been referred to as "host-guest" polymerisation or template polymerisation.

BRIEF DESCRIPTION OF THE FIGURES

The invention will now be described further with reference to the accompanying drawings, in which:

FIG. 4 depicts schematically another molecular imprinting method according to the invention. In the Figure, an imprint of a biomolecule is made by filling the active or binding sites thereof with monomers optionally with crosslinking agents and subsequently using the resultant matrix as a mold or cast in a second imprinting step. This results in the formation of anti-idiotype imprints of the first preformed imprint. In FIG. 4, the particular binding species is immobilized on a matrix (1), which optionally may be degradable, and a polymerization mixture containing functionally complementary monomers, optionally containing crosslinking agents, is added in step A. Following polymerization, the original matrix is dissolved in step B, resulting in the formation of newly-formed polymeric anti-idiotype binding sites (3), which are accessible. The material of (3) can be used to obtain an imprint 4 as depicted in step D.

It has been demonstrated that molecular imprints can serve as mimics of naturally occurring binding sites [5]. Furthermore, such imprints can also be made to form recognition sites of a wide range of compounds. Analogous to anti-idiotype antibodies, the obtained cavities of such original imprints can be used as molds for complementary "daughter imprints" leading to anti-idiotypic imprints or images of the original imprints. The resulting images would resemble the original imprint species in shape and functionality. The principle is schematically described in FIG. 2.

Figure 2:
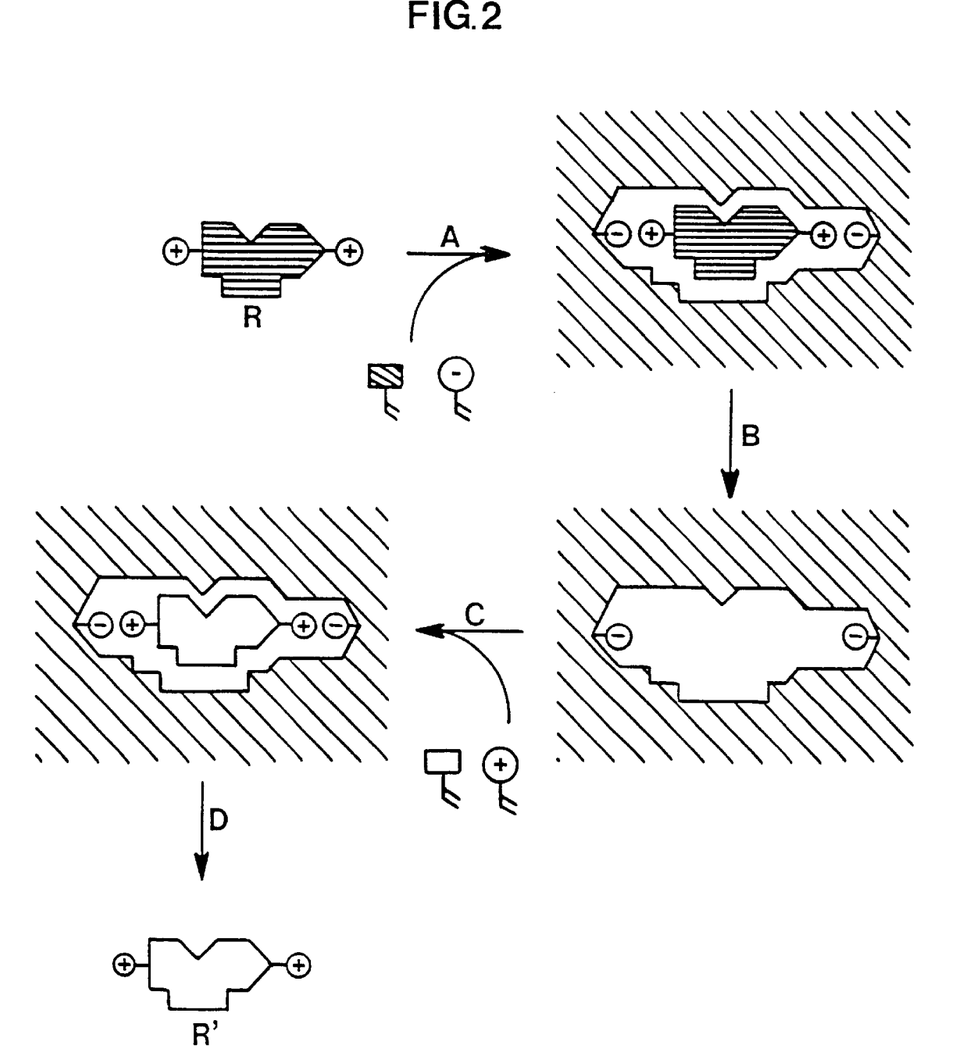
FIG. 2 depicts schematically the production of "daughter imprints" resulting in the formation of anti-idiotypic imprints or images of original imprints by molecular imprinting. In the Figure, R is a compound having a positive charge, A refers to an initial polymerization step using complementary monomers and crosslinking agents. B is a subsequent step comprising the removal of the imprint molecule effected after the initial polymerization, C is a subsequent polymerization, and D refers to a step wherein the original imprint is removed leaving the anti-idiotypic imprint free. R' refers to the obtained molecule or "filler" which possesses a structure complementary to the original imprint molecule.

A molecular imprint is made against a compound, e.g. compound R carrying positive charges, using monomers functionally complementary to the print molecule, e.g. monomers containing negative charges, in step A. The cavities obtained after removal of the imprint molecule (B) are subsequently filled with other complementary functional e.g. polymerisable building stones, e.g. positively charged monomers, and polymerisation is allowed to take place (C). In the following step the original cast or mold which carried the original imprint is removed (D) leaving the anti-idiotypic imprint or imprint of the original imprint free. The obtained molecule, R' which could be called "filler", should resemble or be complementary to the original imprint molecule in shape and functionality, but is, dependent on the "filling material" applied, different in composition than R.

Figure 3:
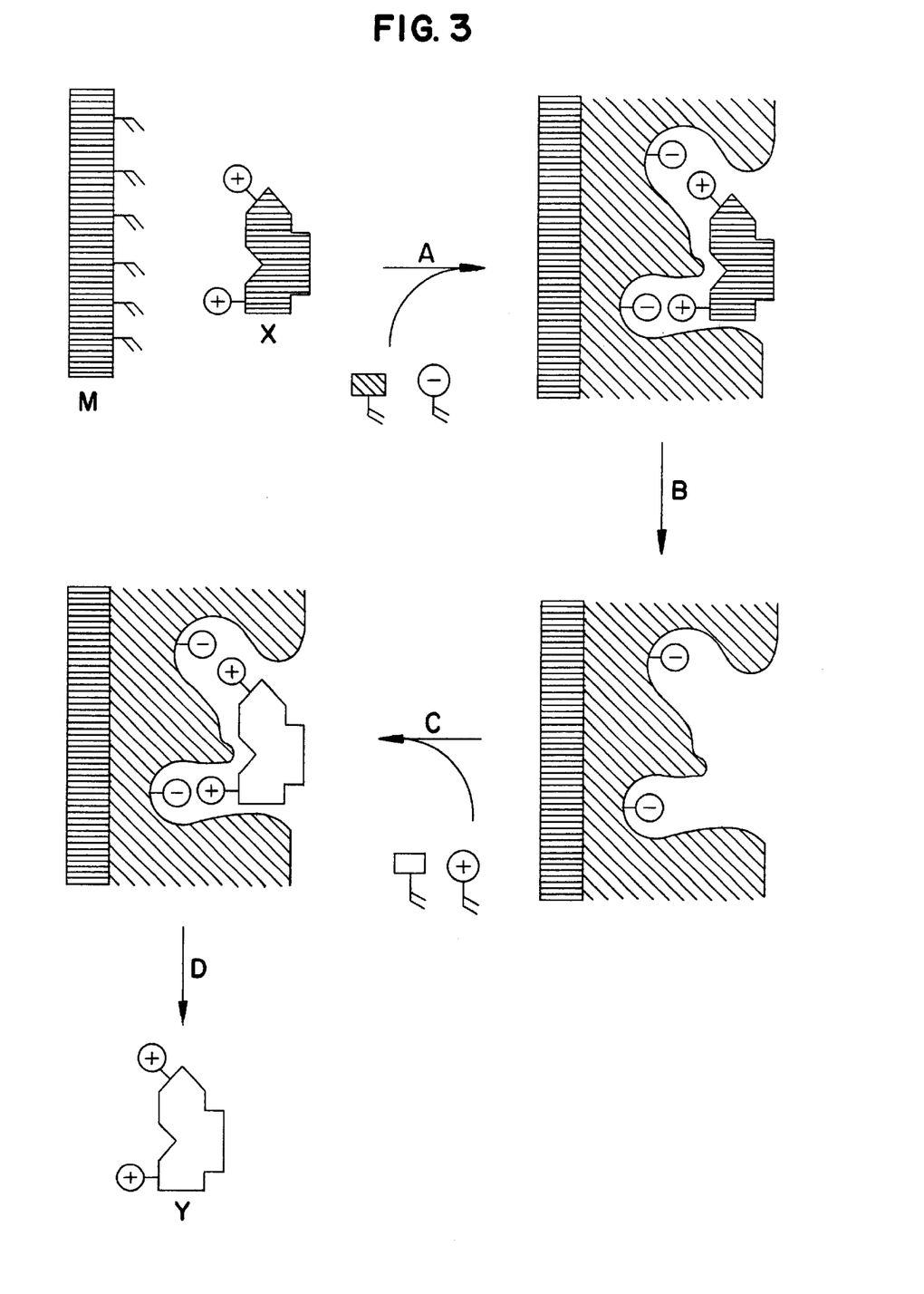
FIG. 3 depicts schematically an imprinting method according to the invention. More specifically, this schematic depicts surface-imprinting using a molecular imprint made against a positively charged compound X. In the Figure, A refers to an initial polymerization step, B refers to an extraction step comprising removal of the print molecule effected after the initial polymerization, C refers to a subsequent polymerization step (which polymerization reaction uses the recognition sites that are complementary in shape and functionality to compound X which were produced in the initial polymerization), and D refers to the subsequent removal of the first polymer resulting in an anti-idiotype imprint polymer (Y) that mimic the structure of the original compound X.

As an extension of the technique one can envisage, what could be called surface-imprinting, the following: (FIG. 3). A molecular imprint is made against a compound, e.g. compound X carrying positive charges. A functionalised matrix (M) carrying polymerisable groups together with complementary monomers, e.g. negatively charged monomers, are utilised in the polymerisation step A. Extraction of the print molecule (B) leaves the polymer with recognition sites complementary in shape and functionality to compound X. Using these sites as molds or casts in a kind of anti-idiotype polymerisation utilising complementary monomers, e.g. positively charged monomers, (C) and subsequent removal of the first polymer (D) renders an anti-idiotype imprint polymer (Y) mimicking the original compound X. Thus, the surface-imprint of the original molecule (X), is prepared which could be employed to create the structurally related molecule (Y). This technique should be especially useful for larger molecules.

One requirement for the envisaged imprint is that both the original matrix as well as the subsequently obtained matrix are capable of allowing imprints to be made. Another requirement is that the original, i.e. the first imprint material, can be removed without interfering with the memorising capability of the second imprint. A number of possible materials and approaches are given in the examples. These include the use of reversibly crosslinking monomers such as the use of crosslinkers containing Shiff's base-linkages [6]. The latter polymers are easily dissolved.

Crosslinkers Containing Shiff's Base-linkages

Another possibility is the use of disulfide containing analogs of bis-acrylamide, e.g. bis-acrylylcystamine, which can be dissolved with 2-mercaptoethanol [7].

Bis-acrylylcystamine

Other crosslinkers that can be cleaved are N,N'-diallyltartardiamide [8] or N,N'-(1,2-dihydroxyethylene)bis-acrylamide [9].

N,N'-diallyltartardiamide

N,N'-(1,2-Dihydroxy)-bisacrylamide

Another possible way is to use completely different matrices as first or second imprints such as agarose or silica, the latter prepared by polymerisation of silanes. As an alternative to the removal of the first imprint by subsequent dissolution of the matrix, the second imprint may be loosened up using such reversibly dissolving monomers whereby care is to be taken to protect the recognising properties of the second imprint matrix. Other approaches facilitating such dissociation include the use of magnetic beads carrying the imprint molecules. Such matrices can, posterior to polymerisation, be separated by application of a magnetic field forcing the matrices apart. Another alternative approach involves the polymerisation at interfaces.

Figure 4:
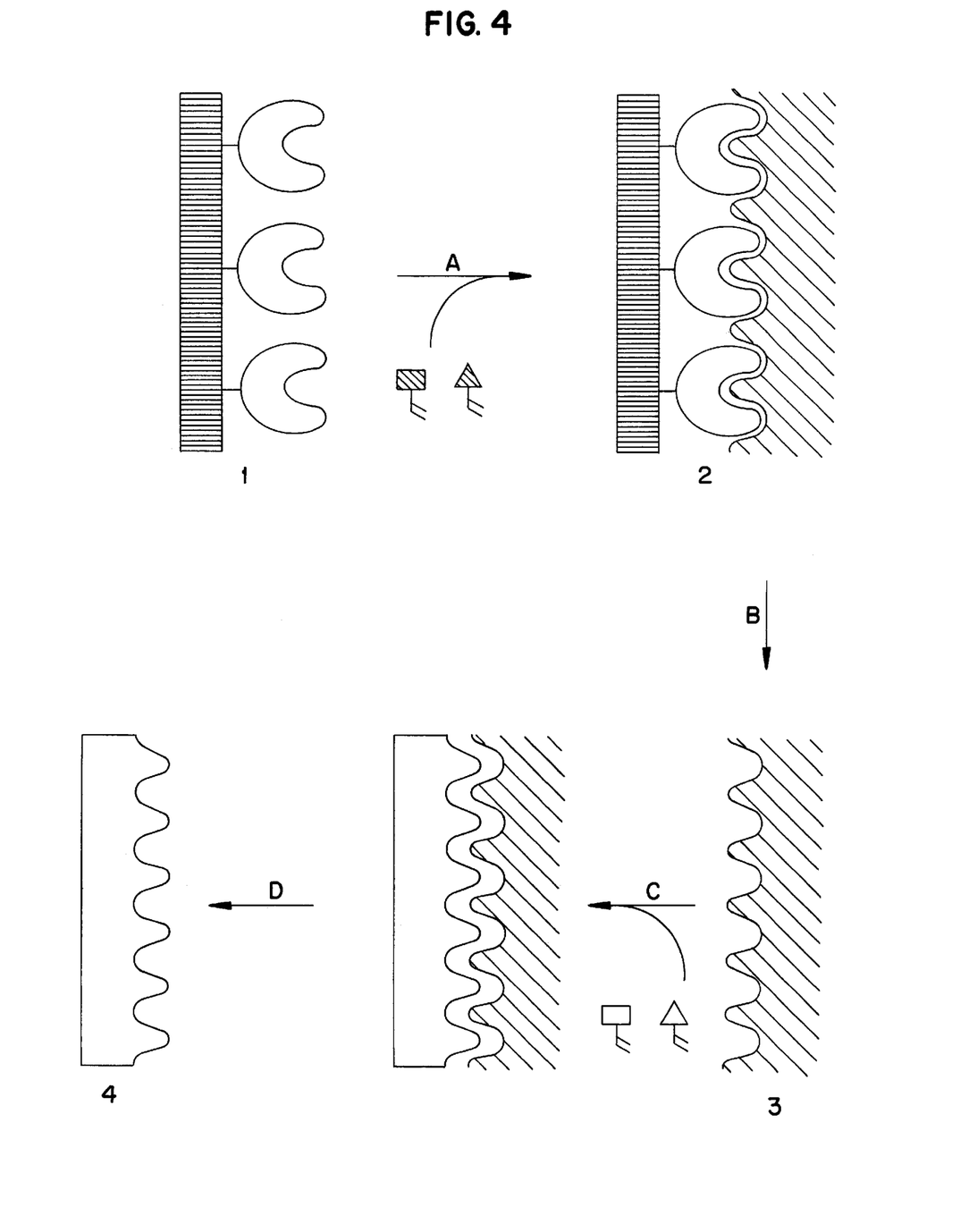

An additional alternative way to obtain imprints would be to directly make imprints of biomolecules by filling the active or binding sites of the latter with monomers and subsequently using the formed matrix as a mold or cast in a second imprinting step. This would lead to the formation of anti-idiotype imprints of the first preformed imprints as depicted in FIG. 4. The particular binding species is immobilised on a degradable matrix (1), e.g., agarose beads, and a polymerisation mixture containing functionally complementary monomers is added in step A. Following polymerisation the original matrix is dissolved in step B making the newly formed polymeric anti-idiotype binding sites (3) accessible. Such preparations could then be used e.g. as artificial inhibitors or receptors either while arranged as a film or thin membrane or in smaller units. Further, as indicated in FIG. 4, one can go from 3 over step C employing the imprint of 3 to obtain via step D a plastic imprint 4 similar to 1.

Figure 5:
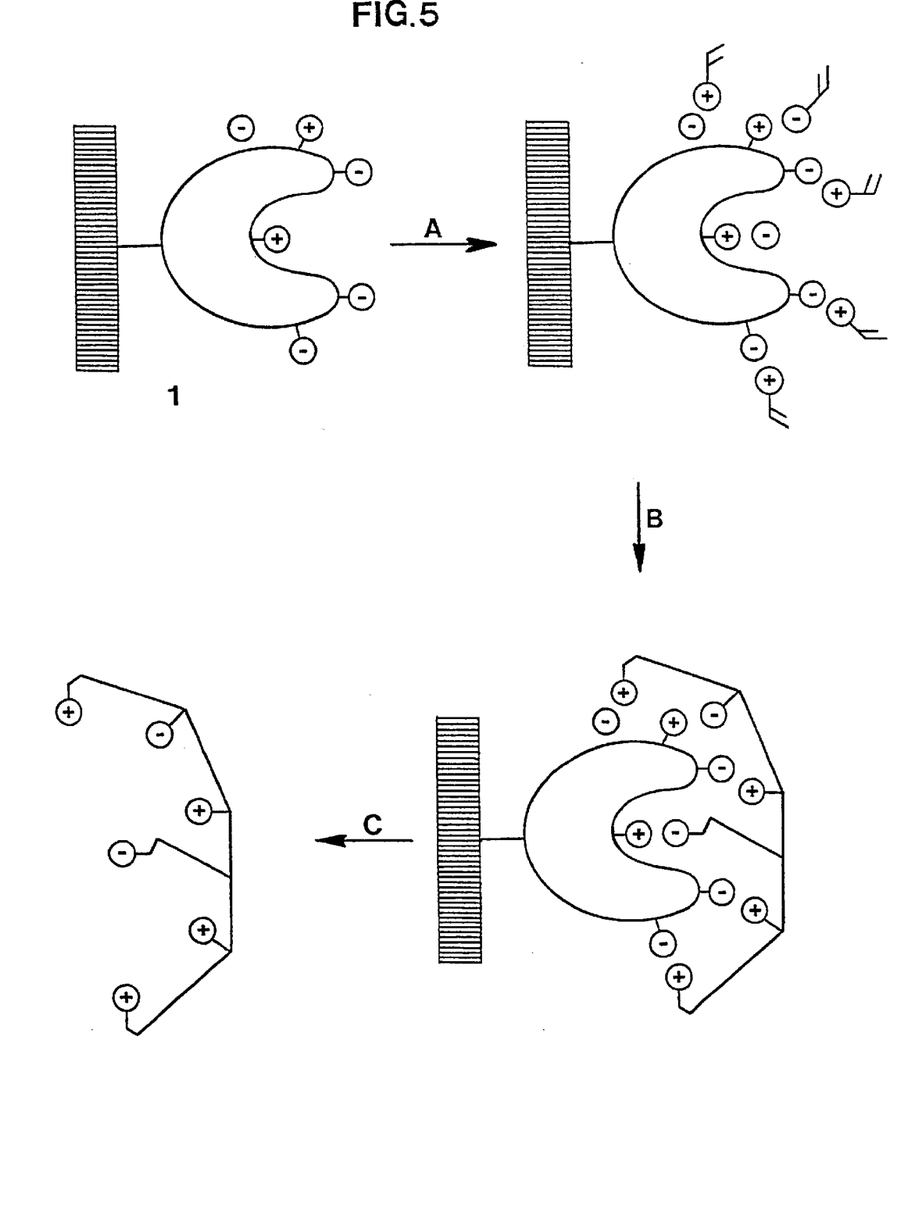
FIG. 5 depicts schematically another imprinting method according to the invention. In the Figure, monomers or other molecules are lined up along a surface or active site of desired molecules, e.g., biomolecules. The former interact with functional groups of the molecule 1, in step A followed by their condensation (B). Thereafter, 1 is removed in step C resulting in the formation of a thin-layer imprint of 1.
Figure 6:
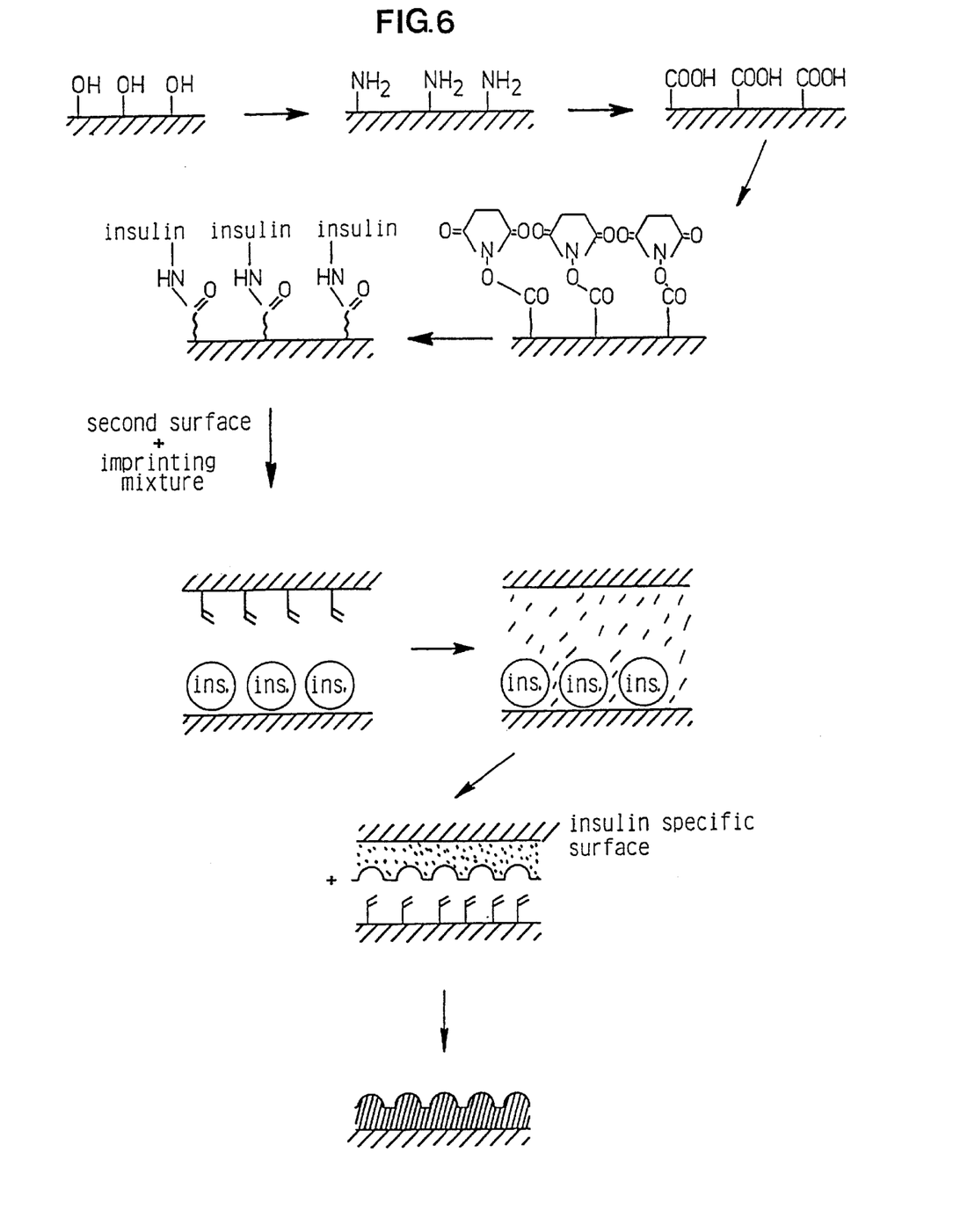
FIG. 6 shows the preparation of an anti-idiotype imprint, preferentially with a further polymerisation (imprinting) system, corresponding to 4 in FIG. 4.

Further, as an alternative to the above direct imprinting, one can envisage the lining up of monomers or other molecules along a surface or active site of e.g. biomolecules as outlined in FIG. 5. The former are allowed to interact with functional groups of the molecule, 1, in step A followed by their condensation (B). Removal of 1 in step C leads to the formation of a thin-layer imprint of 1. Alternatively, the functional groups of the biomolecule are first derivatised followed their condensation.

Potential use of such imprints (=filler molecules)
(1) They could lead to new enzyme inhibitors, new drugs, new affinity ligands, new anti-affinity material including cell-affinity material, anti-antibodies and new catalysts.
(2) They could replace peptides, nucleotides, carbohydrates or other biological material with other material such as organic polymers.
(3) They could lead to new compounds with identical or similar function as the imprint species but being more stable and cheaper to prepare.
(4) In an extension, in cavities or on surfaces obtained by imprinting new enzyme-like catalysts may be obtained.
(5) Such cavities if they are chiral can be used as scaffold to create new chiral molecules.
(6) The cavities obtained from the first imprint can be used to create new molecules utilising combinatorial libraries of various organic or inorganic molecules.
(7) Analogous to anti-idiotype antibodies.

EXAMPLE 1

Acetylcholin can be molecularly imprinted using a modified standard protocol [10]. Thus, acetylcholin is polymerised with methacrylic acid, different types of crosslinkers including those that can be selectively split (e.g. bis-acrylylcystamin) and initiator (azo-isobutyro-nitrile, AIBN) in chloroform. The formed imprints are complementary in shape, charge and hydrogen bonding capabilities to acetylcholin. The imprint molecule is extracted from the polymer using methanol/acetic acid (9:1). Susquently, a cocktail of small polymerisable monomers with or without crosslinkers is added in the formed cavity and allowed to polymerise. Addition of agents to dissolve the formed original matrix, such as SH-carrying compounds, make the daughter imprints become accessible. The binding capabilities of the obtained anti-idiotype analogues of acetylcholin could be tested in competition assay against free acetylcholin.

EXAMPLE 2

A molecular imprint against the trypsin inhibitor p-aminobenzamidin is prepared. The imprint species is polymerised with appropriate monomers, e.g. methacrylic acid and breakable crosslinkers, e.g. bis-acrylylcystamine. Following extraction of p-aminobenzamidin, an anti-idiotype imprint is made using the p-aminobenzamidin imprint material as a cast in a new polymerisation step. The original imprint material is dissolved leaving the mirror imprint material free for application. The formed anti-idiotype imprint material, mimicking the trypsin inhibitor, can subsequently be analysed in an affinity assay against trypsin or in a competition assay against large trypsin inhibitors like bovine pancreatic trypsin inhibitor (BPTI).

EXAMPLE 3

Trypsin is immobilsed on agarose beads. Anti-idiotype imprints of trypsin are prepared similar to the preceding examples by polymerisation of an appropriate monomeric cocktail and suitably crosslinkers on the surface of the agarose beads. Addition of an acidic solution leads to dissolution of the agarose beads thus making the anti-idiotype imprints accessible. Analysis can be perceived using the anti-idiotype imprint material as an affinity matrix for trypsin.

EXAMPLE 4

A silicon surface or microslide was first oxidised and then silanised with aminopropyl triethoxy silane in aqueous solution overnight. The slides were then treated overnight with succinic anhydride at pH 6 which leaves only free carboxyl groups at the surface. In the next step the slides were extensively washed with dioxane to obtain anhydrous conditions and reacted with N-hydroxysuccinimide and N,N'-dicyclohexylcarbodiimide in dioxan for 2 h which converts the carboxyl groups to N-hydroxysuccinimid esters. After further washing, the slides were treated with insulin in 0.1 M NaHCO$_3$ buffer pH 9.2 overnight. Under these conditions the amino group of lysine B29 react specifically with the N-hydroxysuccinimide ester. Alternatively the coupling could be achieved at pH 6.4 via the terminal amino groups of B1 phenylalanine.

Determination of the amount of bound insulin was carried out by ellipsometry.

Insulin possesses a surface, zinc binding histidine at B10 on the opposite side of the structure from the immobilisation site (B29) (B1 et al, Biopolymers 23 (1984), 391–395). There are five other basic amino acids at the surface which are positively charged below the isoelectric point of 5.5 and will associate with sulphonate groups (Matsuura et al., JACS 115 (1993), 1261–1264). Thus, imprinting can be carried out with i) an aqueous solution of the chelating monomer N-(5-methacrylamido-1-carboxypentyl)iminodiacetic acid, CuSO$_4$, styrene sulphonate, acrylamide and piperazine-bisacrylamide at pH 4 and 5° C. using methylene blue as photoinitiator, or ii) an organic solution of N-(4-vinyl)-benzyl iminodiacetic acid (VBIDA), CuSO$_4$, methacrylic acid (MAA) and ethylene glycol dimethacrylate (EGDMA) and using AIBN as initiator.

The imprinting forms a stable film, which can be separated from the surface on which it has been formed, e.g. manually or by dissolution.

The immobilised insulin was shown to promote lipogenesis by fat cells in a bioassay.

EXAMPLE 5

According to similar processes as described in Example 4, penicillin G was coupled to a microslide by a) Acrylate derivatisation. A sol of 1 Wt % of 3-(triethoxysilylpropyl)methacrylate in dry acetone is allowed to react with the slides by established procedures, b) Amino derivatisation. To wet slides are added amino silane sol (10% aminopropyl triethoxysilane in H$_2$O-pH adjusted to 3.5). 8.8 mg penicillin G, 25 mg EDAC, 25 ml ⓟ pH 7.0 are dissolved, left at room temperature for 30 min, followed by addition of the amino slides (4 per Petri dish, spread out), 2 ml penicillin G-coupling sol is added to each slide, ensuring that it covers the slide completely, and lefts overnight at room temperature.

EXAMPLE 6

According to a process similar to the one described in Example 5, theophyllin was coupled to microslides.

References

1. N. K. Jerne, Ann. Immunol. 125, 373–378 (1974).
2. L. Izadyar, A. Friboulet; M. H. Remy, A. Roseto, D. Thomas, Proc. Natl. Acad. Sci. USA 90, 8876–8880 (1993).
3. K. Mosbach, U.S. Patent No. 5,110,833, (1992).
4. B. Ekberg, K. Mosbach, Trends Biotech. 7, 92–96 (1989).
5. G. Vlatakis, L. I. Andersson, E. Müller, K. Mosbach, in Nature, (1993) 645–647.
6. H. Ringsdorf, G. Greber, Makromol. Chem. 25, 237–239 (1958).
7. J. N. Hansen, Anal. Biochem. 76, 37–44 (1976).
8. P. J. Spaeth, H. Koblet, Anal. Biochem. 93, 275–285 (1979).
9. P. B. H. O'Connell, C. J. Brady, Anal. Biochem., 63–73 (1976).
10. D. J. O'Shannessy, B. Ekberg, L. I. Andersson, K. Mosbach, J. Chromatogr. 470, 391–399 (1989).

What is claimed is:

1. A method of producing a molecular imprint of an artificial or native molecule, comprising the following steps:

(1) polymerizing a mixture comprising monomers and crosslinkers in the presence of a molecule for which a molecular imprint is to be produced, thereby forming a matrix comprising an imprint of the molecule;

(2) separating the molecule from the matrix;

(3) polymerizing in a subsequent step a mixture of monomers and crosslinkers which are the same or different from the monomers and crosslinkers utilized in the first polymerization step, wherein polymerization is conducted in the imprint in the matrix, thereby creating a molecular imprint of the molecule, which molecular imprint possesses the same functionality and/or shape as said molecule; and (4) separating the resultant molecular imprint from the imprint in the matrix.

2. A method of producing a molecular imprint of surface bound artificial or native molecules comprising the following steps:

(1) polymerizing a mixture of monomers and crosslinkers resulting in the formation of a film having imprints of the surface bound molecules;

(2) separating the imprinted film from the surface bound molecules;

(3) polymerizing a second mixture of monomers and crosslinkers which are the same or different from the monomers and crosslinkers utilized in the first polymerization step on the imprinted film, thereby producing a molecular imprint of the surface bound molecules which possesses the same functionality and/or shape as the surface bound molecules; and (4) removing the resultant molecularly imprinted film from the imprinted film.

3. A method of producing a molecular imprint of surface bound artificial or native molecules comprising the following steps:

(1) polymerizing a mixture of monomers and crosslinkers by a method which results in the formation of a film having molecular imprints of surface bound molecules; and (2) separating the resulting molecularly imprinted film from the surface bound molecules.

4. The method according to claim 1, wherein the artificial or native molecule used to produce the molecular imprint is selected from the group consisting of compounds having moieties comprising artificial or natural binding sites.

5. The method according to claim 4, wherein said compounds having moieties comprising artificial or natural binding sites are selected from the group consisting of nucleotides, receptors, antibodies, enzymes, catalysts and molecular imprints of said compounds.

6. The method according to claim 2, wherein the artificial or native molecule used to produce the molecular imprint is selected from the group consisting of compounds having moieties comprising artificial or natural binding sites.

7. The method according to claim 6, wherein said compounds having moieties comprising artificial or natural binding sites are selected from the group consisting of nucleotides, receptors, antibodies, enzymes, catalysts and molecular imprints of said compounds.

8. The method according to claim 3, wherein the artificial or native molecule used to produce the molecular imprint is selected from the group consisting of compounds having moieties comprising artificial or natural binding sites.

9. The method according to claim 8, wherein said compounds having moieties comprising artificial or natural binding sites are selected from the group consisting of nucleotides, receptors, antibodies, enzymes, catalysts and molecular imprints of said compounds.

10. A method for producing an anti-idiotypic molecular imprint of a molecule having artificial or natural binding sites comprising polymerizing a mixture of monomers and crosslinkers within the cavities produced by the molecular imprinting of molecules possessing artificial or natural binding sites, wherein the monomers and crosslinkers become oriented within said binding sites prior to polymerization thereby forming, upon polymerization, a compound which is an anti-idiotype of the original imprint molecule.

11. The method of claim 10, wherein the monomers are selected from the group consisting of acrylic monomers, silanes and azides.

12. A method for the production of anti-idiotypic compounds which are molecular imprints of artificial or native molecules which comprises forming, by the polymerization of monomers and crosslinkers, a molecular imprint of a previously synthesized molecular imprint.

13. The method according to claim 12, wherein the molecular imprints of the artificial or native molecules are selected from the group consisting of inhibitors, drugs, affinity ligands, antibodies, enzymes, catalysts, nucleotides and receptors.

14. A method for the production of an anti-idiotypic molecular imprint, comprising forming, by the polymerization of monomers and crosslinkers, chiral cavities from non-chiral basic compounds or chiral monomers, thereby forming said anti-idiotypic molecular imprint.

15. The method according to claim 1 or 2, wherein the molecular imprint produced is selected from the group consisting of inhibitors, drugs, affinity ligands, anti-affinity materials, anti-antibodies, nucleotides, antigens, enzymes and catalysts.

16. The method according to claim 15, wherein said anti-affinity material is a cell-affinity material.

17. A molecular imprinting method which results in the formation of a molecule selected from the group consisting of inhibitors, drugs, affinity ligands, antibodies, anti-affinity materials, nucleotides, antigens, enzymes and catalysts, which method comprises the following steps:

(1) producing a molecular imprint by polymerizing monomers and crosslinkers in the presence of a molecule selected from the group consisting of inhibitors, drugs, affinity ligands, antibodies, anti-affinity materials, nucleotides, antigens, enzymes and catalysts, thereby producing a matrix comprising an imprint of the molecule;

(2) separating the molecule from the matrix;

(3) polymerizing in a subsequent step a mixture of monomers and crosslinkers which are the same or different from the monomers and crosslinkers utilized in the first polymerization step, wherein polymerization is conducted in the imprint in the matrix, thereby creating a molecular imprint of the molecule, which molecular imprint possesses the same functionality and/or shape as said molecule; and (4) separating the resultant molecular imprint from the imprint in the matrix, thereby producing a molecular imprint which is a compound selected from the group consisting of inhibitors, drugs, affinity ligands, antibodies, anti-affinity materials, nucleotides, antigens, enzymes and catalysts.

18. The method according to claim 7, wherein said anti-affinity material produced by said method is a cell-affinity material.

19. The method of claim 1 or 17, where in step (4) the molecular imprint is separated from the imprint in the matrix by dissolution of said matrix.

20. The method of claim 1 or 17, where in step (2) the molecule is separated from the matrix by dissolution of the matrix.

21. The method of claim 1 or 17, wherein the imprint molecule is comprised of a magnetic bead and the imprint molecule is separated from the matrix in step (2) by application of a magnetic field.

22. The method of claim 1 or 17, wherein the molecule that is imprinted is a protease inhibitor.

23. The method of claim 1 or 17, wherein the molecule that is imprinted is acetylcholine.

24. The method of claim 2 or 3, wherein the film is produced on a microslide.

* * * * *